United States Patent
Selman-Housein Sosa

(10) Patent No.: US 8,211,947 B2
(45) Date of Patent: Jul. 3, 2012

(54) COMPOSITION AND METHOD FOR TREATING AND PREVENTING MUSCULOSKELETAL AND CONNECTIVE TISSUE DISORDERS

(76) Inventor: Guillermo Selman-Housein Sosa, Toronto (CA)

(*) Notice: Subject to any disclaimer, the term of this patent is extended or adjusted under 35 U.S.C. 154(b) by 8 days.

(21) Appl. No.: 12/021,208

(22) Filed: Jan. 28, 2008

(65) Prior Publication Data
US 2009/0192201 A1 Jul. 30, 2009

(51) Int. Cl.
*A61K 31/44* (2006.01)
*A61K 31/22* (2006.01)
*A61K 31/20* (2006.01)
*A01N 45/00* (2006.01)
*A01N 37/36* (2006.01)

(52) U.S. Cl. ........ 514/825; 514/166; 514/168; 514/929; 514/355; 514/546; 514/560; 514/356

(58) Field of Classification Search ................ 514/825, 514/166, 168, 929, 355, 558, 547, 546, 560, 514/356
See application file for complete search history.

(56) References Cited

U.S. PATENT DOCUMENTS

| | | | | |
|---|---|---|---|---|
| 4,725,609 A | * | 2/1988 | Kull et al. | 514/355 |
| 4,879,312 A | * | 11/1989 | Kamarei et al. | 514/560 |
| 4,965,252 A | * | 10/1990 | Kuhrts | 514/54 |
| 5,180,747 A | * | 1/1993 | Matsuda et al. | 514/681 |
| 6,015,821 A | * | 1/2000 | Horrobin et al. | 514/355 |
| 2002/0025983 A1 | * | 2/2002 | Horrobin | 514/560 |
| 2004/0116498 A1 | * | 6/2004 | Husband | 514/408 |
| 2004/0191294 A1 | * | 9/2004 | Ramaprasad et al. | 424/439 |
| 2005/0107294 A1 | * | 5/2005 | Acosta et al. | 514/12 |

OTHER PUBLICATIONS http://web.archive.org/web/20060913022822/http://www.omega-3.se/en/food.html, food that is rich in omega-3, Sep. 2006.*
www.nutrition.org, n-3 fatty acids and health 2007.*
Diepenbrocket et al, Genetic Regulatin of linolenic acid concentration in rapeseed, abstract, Crop science, 27: 75-77, 1987. abstract only.*
Silva ( Vitamin, K, An arthritis preventative Home remedy, article in home remedy cures, date published Jun. 13, 2006, Retrieved from the internet on Nov. 20, 2010, URL: http://www.holisticjunction.com/diplayarticle.fcm?ID-6154.*
Shikha ( Omega-3 in rheumatoid arthritis: A brief review, published Jun. 19, 2006, retrieved from the internet on Nov. 20, 2010, URL: http://www.Shvoong.com/medicine-and-health/253904-omega-rheumatoid-arthritis-brief.*
Vitamin B3-niacin article (dated Jan. 2006, retrieved from the internet on Nov. 20, 2010, URL: http://web.archive.org/web/20060114023746/http://www.vitamins-supplements.org/vitamin.*
Aaseth et al. Analyst, Jan. 1998, vol. 123 (3-6).*

* cited by examiner

*Primary Examiner* — Savitha Rao

(57) ABSTRACT

The present invention relates to a pharmaceutical composition and method for treating and preventing musculoskeletal and connective tissue diseases of unknown etiology, such as different forms of arthritis and other rheumatic conditions, comprising a combination of therapeutic agents that improve the processes of blood circulation and angiogenesis in the affected tissues, as well as other supporting therapies. Among the components of herein proposed pharmaceutical composition, are: vitamin K, polyunsaturated fatty acids (blood thinner), and niacin (vasodilator and hypolipidemic agent).

14 Claims, No Drawings

COMPOSITION AND METHOD FOR TREATING AND PREVENTING MUSCULOSKELETAL AND CONNECTIVE TISSUE DISORDERS

FIELD OF THE INVENTION

The present invention relates generally to a pharmaceutical composition, comprising a combination of therapeutic agents that improve the processes of blood circulation and angiogenesis. Among the herein proposed therapeutic agents are: vitamin K, polyunsaturated fatty acids (blood thinner), and niacin (vasodilator and hypolipidemic agent). Other supporting therapies that do not interfere with the above mentioned processes could also be used in combination with herein proposed composition for treating and preventing musculoskeletal and connective tissue diseases of unknown etiology, such as different forms of arthritis and other rheumatic conditions.

BACKGROUND OF THE INVENTION

Rheumatic diseases are the most common chronic musculoskeletal diseases. These diseases are different individual illnesses with differential features, treatments, complications, and prognoses. They are similar in that they have a tendency to affect the joints, muscles, ligaments, cartilage and tendons, and many have the potential to affect internal body areas (The Merck Manual, 17th edition, 1999, Merck & Co., Inc).

While inflammation is one symptom of chronic musculoskeletal diseases, the pain and stiffness of the joints and muscles is particularly debilitating, as this physically inhibits movement and lessens the motivation for daily activities. Thus, these diseases may become a disabling conditions. Most of these diseases are chronic, progressive, and require long-term medication.

Arthritis is classified as one of the rheumatic diseases. It is a disorder featuring chronic inflammation of joints. There are over one hundred forms of arthritis, which range from those related to wear and tear of cartilage (such as osteoarthritis) to those associated with inflammation resulting from an overactive immune system (such as rheumatoid arthritis). Arthritis sufferers include men and women, children and adults. Approximately 350 million people worldwide have arthritis, and this figure increases by hundreds of thousands every year.

Causes of arthritis include injury (leading to osteoarthritis), abnormal metabolism (such as gout and pseudogout), inheritance, infections, as well as for unclear reasons (such as Rheumatoid arthritis and Systemic lupus erythematosus).

Symptoms of an established arthritis condition include pain and limited function of joints. Inflammation of the joints from arthritis is characterized by joint stiffness, swelling, redness, and warmth. Tenderness of the inflamed joint can be present, as well as fever, fatigue and even symptoms from abnormalities of organs such as the lungs, heart, or kidneys.

It has been estimated that the total cost of the arthritis bill for the United States, in terms of hospitalizations, doctor visits, medications, physical therapies, nursing home care, lost wages, early death, and family discord is over $50 billion dollars annually. The CDC's National Center for Chronic Disease Prevention and Health Promotion has concluded that the total costs attributable to arthritis and other rheumatic conditions (AORC) in the United States in 2003 was approximately $128 billion. This equaled 1.2% of the 2003 U.S. gross domestic product. National medical costs attributable to AORC grew by 24% between 1997 and 2003. This rise in medical costs resulted from an increase in the number of people with AORC (Yelin E., Murphy L., Cisternas M. G., Foreman A. J., Pasta D. J., Helmick C. G. Medical Care Expenditures and Earnings Losses of Persons with Arthritis and Other Rheumatic Conditions in 2003 with Comparisons to 1997. Arthritis Rheum. 2007, 56(5):1397-1407).

Rheumatoid arthritis and osteoarthritis are the two major forms of arthritis.

Rheumatoid arthritis (RA) is a chronic, systemic disease characterized by an inflammatory, erosive synovitis. Its pathological diagnosis is hyperplasia of synoviocytes, hyperaemia, thickening of blood vessel walls, infiltration of inflammatory cells, hyperplasia, transparency, and degeneration of fibrotic tissues. Changes in the synovium are marked by the formation of new blood vessels (termed angiogenesis), which play a key role in the formation and maintenance of a pannus of inflammatory vascular tissue. This pannus covers and erodes articular cartilage, eventually leading to joint destruction. The etiology of RA is unknown. Pathogens, environmental and genetics factors among others have been associated as responsible for triggering an uncontrolled immune reaction. According to theory of "mistaken identity", an offending organism causes an immune response that leaves behind antibodies that are specific to that organism. However, the antibodies are not specific enough, and they will begin an immune attack against the synovium, because some molecule in the synovium "looks like" a molecule on the offending organism that created the initial immune reaction. Thus, rheumatoid arthritis is considered an autoimmune disorder associated with a pathological angiogenesis of affected tissues. (William P A. The pathophysiology and treatment of rheumatoid arthritis. Arthritis Rheumatism 1997, 40(4): 585-597; Paleolog E. M. Angiogenesis in rheumatoid arthritis. Arthritis Res. 2002, 4(3):S81-S90).

The symptoms that distinguish rheumatoid arthritis from other forms of arthritis are inflammation and soft-tissue swelling of many joints at the same time (polyarthritis). Typically, the joints are initially affected asymmetrically, and then in a symmetrical fashion as the disease progresses. The pain generally improves with use of the affected joints, and usually, there is stiffness of all joints in the morning that lasts over one hour. Thus, the pain of rheumatoid arthritis is usually worse in the morning compared to the classic pain of osteoarthritis, where the pain worsens over the day as the joints are used. Extra-articular manifestations also distinguish this disease from osteoarthritis. For example, most patients also suffer with anemia, either as a consequence of the disease itself or as a consequence of gastrointestinal bleeding as a side effect of drugs used in treatment, especially NSAIDs (non-steroidal anti-inflammatory drugs) used for analgesia.

Rheumatoid arthritis is a disabling and painful inflammatory condition, which can lead to substantial loss of mobility due to pain and joint destruction. RA is a systemic disease, often affecting extra-articular tissues throughout the body including the skin, blood vessels, heart, lungs, and muscles. The course of the disease varies greatly from patient to patient. Some patients have mild short-term symptoms, but in most, the disease is progressive for life. About 60% of RA patients will be unable to work 10 years after the onset of the disease and their quality of life will be severely reduced (Tammi L. Shlotzhauer, M. D., James L. McGuire, M. D. Living with Rheumatoid Arthritis. Johns Hopkins University. 2nd ed. 2003, 312 pp).

Rheumatoid arthritis is one of the top five common human diseases. World Health Organization estimated that RA affects 1% of the human population on earth. Approximately 2.1 million Americans suffer from rheumatoid arthritis. The incidence of RA is in the region of 3 cases per 10,000 population per annum. Onset is uncommon under the age of 15 and from then on the incidence increases with age until the age of 80. The prevalence rate is 1%, with women affected three to five times as often as men. It is 4 times more common in smokers than non-smokers. There are also racial differences: some Native American groups have higher prevalence rates (5-6%), while black persons from the Caribbean region have lower prevalence rates.

Osteoarthritis (OA) is a chronic disease of the joints, especially the weight-bearing joints, that develops when the lining of joints degenerates, leading to lipping and spurring of bones, pain, and decreased mobility and function. Osteoarthritis, is also known as hypertrophic arthritis, degenerative arthritis, degenerative joint disease, proliferative arthritis or osteoarthrosis (The Merck Manual, 17th edition, 1999, Merck & Co., Inc).

The cause of osteoarthritis is not entirely clear, however, it may be a combined result of mechanical impairment and physiological alterations with aging, as well as other factors such as obesity, bone density, injury and genetics. The onset of OA is gradual and most often affects the hips, knees, fingers, and spine, although other joints may be involved. Pain is the main symptom, which usually worsens with exercise and is relieved by rest. Morning stiffness is also common and diminishes with movement. As OA progresses, joint motion is lost, and tenderness and grating sensations may develop. OA of the spine may lead to shooting pains down the arms or legs (Kenneth D. Brandt M D. 2005. Diagnosis and Nonsurgical Management of Osteoarthritis, ed: Professional Communications Incorporated, Caddo Okla., 384 pages).

Osteoarthritis is classified as non-inflammatory arthritis. However, recent research shows that although there is usually no appreciable swelling in the early stage of the disease, as the arthritis progresses the inflammation process takes place (Roach H. I., Aigner T., Soder S., Haag J., Welkerling H. Pathobiology of osteoarthritis: pathomechanisms and potential therapeutic targets. Curr Drug Targets. 2007, 8(2):271-282.). In osteoarthritis, the top layer of cartilage breaks down and wears away. This allows bones under the cartilage to rub together. The rubbing causes pain, swelling, and loss of motion of the joint. Over time, the joint may lose its normal shape. Also, bone spurs may grow on the edges of the joint. Bits of bone or cartilage can break off and float inside the joint space, causing more pain and damage.

Damage due to OA progresses over time and may result in several problems. The person may have pain, especially when moving a joint. Sometimes, a grating sound can be heard when the roughened cartilage on the surfaces of the bones rub together. Bumps or swelling may appear, especially on the fingers and feet. A joint may feel sore and stiff, and the joint will not move as easily or as far as it once did. All these changes can make it hard to move around and to do everyday tasks. People with osteoarthritis often have joint pain and reduced motion. Advanced OA is a disabling condition.

OA is the most common type of arthritis, especially among elders; 50% of people over age 50 and 80% of people over age 55 have some clinical symptoms of this disease. People that are over 65 generally suffer from OA. More than 21 million Americans have osteoarthritis.

Generally speaking, the process of clinically detectable osteoarthritis is irreversible, and typical treatment consists of medication or other interventions that can reduce the pain of OA, and thereby improve the function of the joint. Therapies that manage osteoarthritis pain and improve function include exercise, weight control, rest, pain relief, alternative therapies and surgery (The Merck Manual, 17th edition, 1999, Merck & Co., Inc).

For rheumatoid arthritis, the basic goal of treatment is to reduce pain and inflammation; to prevent deformation of bone, cartilage, and soft tissues; and to maintain the normal function of the joints; thereby maintaining the normal daily activities of the patients for the longest possible period.

Pharmacological treatment of RA can be divided into disease-modifying antirheumatic drugs (DMARDs), anti-inflammatory agents and analgesics (O'Dell J. Therapeutic strategies for rheumatoid arthritis. N Engl J Med, 2004, 350 (25): 2591-2602). DMARDs have been found to produce durable remissions and delay or halt disease progression through their cytotoxic and/or immunosuppressive properties. In particular, they prevent bone and joint damage from occurring secondary to the uncontrolled inflammation (Vital E., Emery P. Advances in the treatment of early rheumatoid arthritis. Am Fam Physician. 2005, 72 (6): 1002-1004). This is important, as such damage is usually irreversible. Anti-inflammatories and analgesics improve pain and stiffness but do not prevent joint damage or slow the disease progression.

DMARDs can be subdivided into traditional small molecular mass drugs synthesized chemically (azathioprine, cyclosporine A, D-penicillamine, gold salts, hydroxychloroquine, leflunomide, methotrexate (MTX), minocycline and sulfasalazine (SSZ)), and newer biological agents with immuno-modulatory properties, produced through genetic engineering such as: tumor necrosis factor alpha (TNFa) blockers (etanercept, infliximab, adalimumab), interleukin-1 blockers (anakinra), anti-B cell (CD20) antibody (rituximab), blockers of T cell activation (abatacept), etc. (Hasler P. Biological therapies directed against cells in autoimmune disease. Springer Semin Immunopathol. 2006, 27 (4): 443-456; Dombrecht E. J., Aerts N. E., Schuerwegh A. J., Hagendorens M. M., Ebo D. G., Van Offel J. F., Bridts C. H., Stevens W. J., De Clerck L. S. Influence of anti-tumor necrosis factor therapy (Adalimumab) on regulatory T cells and dendritic cells in rheumatoid arthritis. Clin Exp Rheumatol. 2006, 24(1):31-37). It has also been proposed that systemically using interleukin-4 (IL-4), it is possible to arrest the clinical progression of collagen-induced arthritis (CIA), a mouse model for human rheumatoid arthritis, and effectively protect against cartilage and bone destruction (Joosten L. A., Lubberts E., Helsen M. M., Saxne T., Coenen-de Roo C. J., Heinegård D., van den Berg W. B. Protection against cartilage and bone destruction by systemic interleukin-4 treatment in established murine type II collagen-induced arthritis. Arthritis Res. 1999, 1(1):81-91; U.S. Pat. No. 5,955,315; U.S. Pat. No. 5,951,973). IL-4 stimulates proliferation, differentiation and activation of several cell types, including fibroblasts, endothelial cells and epithelial cells. IL-4 is also known to be a potent anti-inflammatory cytokine that acts by inhibiting the synthesis of pro-inflammatory cytokines such as IL-1, TNF-alpha, IL-6, IL-8 and IL-12 by macrophages and monocytes. Moreover, IL-4 stimulates the synthesis of several cytokine inhibitors such as interleukin-1 receptor antagonist (IL-1Ra), soluble IL-1-receptor type II, and TNF receptors. IL-4 suppresses metalloproteinase production and stimulates tissue inhibitors of metalloproteinase-1 production in human mononuclear phagocytes and cartilage explants, indicating a protective effect of IL-4 towards extracellular matrix degradation. Furthermore, IL-4 inhibits both osteoclast activity and survival, and thereby blocks bone resorption in vitro.

Although DMARDs can be effective to improve prognosis of RA, this class of drugs has many serious side effects, and often, they are not tolerated by patients. The most important and most common adverse events relate to liver and bone marrow toxicity (MTX, SSZ, leflunomide, azathioprine, gold compounds, D-penicillamine), renal toxicity (cyclosporine A, parenteral gold salts, D-penicillamine), pneumonitis (MTX), allergic skin reactions (gold compounds, SSZ), autoimmunity (D-penicillamine, SSZ, minocycline), ocular toxicity (hydroxychloroquine) and infections (azathioprine, cyclosporine A).

More recently, there have been emerging new therapies based on $CD25^+$ T regulatory cells (Treg cells). Treg cells are a naturally occurring suppressor T-cell population that regulates a wide variety of immune responses. A major function of $CD25^+$ Treg cells is to inhibit the activity of self-reactive T cells that can potentially cause autoimmune disease (Zwar T. D., van Driel I. R., Gleeson P. A. Guarding the immune system: suppression of autoimmunity by $CD4^+$ $CD25^+$ immunoregulatory T cells. Immunol Cell Biol. 2006, 84(6): 487-501; Suri-Payer E, Fritzsching B. Regulatory T cells in experimental autoimmune disease. Springer Semin Immunopathol. 2006, 28(1):3-16). It has been shown in different experimental models that Treg-cell-based therapies could improve clinical and laboratory variables in CIA, being a very promising therapeutic approach to target the pathogenic mechanism of autoimmune arthritis (Gonzalez-Rey E, Femandez-Martin A, Chorny A, Delgado M. Vasoactive intestinal peptide induces CD4+, CD25+T regulatory cells with therapeutic effect in collagen-induced arthritis. Arthritis Rheum. 2006, 54(3):864-876; Toh M. L., Miossec P. The role of T cells in rheumatoid arthritis: new subsets and new targets. Curr Opin Rheumatol. 2007, 19(3):284-288). Other cell therapies under development for treating rheumatic diseases are: T-cell vaccination (Chen G., Li N., Zang Y. C., Zhang D., He D., Feng G., Ni L., Xu R., Wang L., Shen B., Zhang J. Z. Vaccination with selected synovial T cells in rheumatoid arthritis. Arthritis Rheum. 2007, 56(2):453-463), and therapy using mesenchymal stem cells (Augello A, Tasso R, Negrini S M, Cancedda R, Pennesi G. Cell therapy using allogeneic bone marrow mesenchymal stem cells prevents tissue damage in collagen-induced arthritis. Arthritis Rheum. 2007, 56(4):1175-1186).

Anti-inflammatory agents for treatment of RA or OA include: non-steroidal anti-inflammatory drugs (NSAIDs, most also act as analgesics) and glucocorticoids.

NSAIDs are the major anti-arthritis drugs. They reduce inflammation and pain in the early stage of the disease by inhibiting cyclooxygenase (COX), and therefore the production of prostaglandins (PG), which play a central role in inflammation and pain (Green G A. Understanding NSAIDS: from aspirin to COX-2. Clin Cornerstone. 2001, 3:50-59). The NSAIDs are effective in treating the symptoms of the acute arthritis, but have little effect on preventing the progression of the disease. High doses are often required. Currently, there are many kinds of drug like this, namely acemetacin, diclofenac, ibuprofen, indomethacin, meloxicam, ketoprofen, sulindac, auranofin, naproxen, nabumetone, piroxicam, mecolfenamic acid, chlofenamic acid, mefenamic acid, pirprofen, fenbufen, tolmetin, flufenamide acid, fenoprofen, methocarbamol and nimesulide. NSAIDs are the first-line anti-arthritis drugs and are critical in treating arthritis, however, their effectiveness in treating arthritis remains controversial among the doctors and patients. Moreover, their severe adverse effects cannot be overlooked because the drugs listed above inhibit the production of COX-1 and COX-2 simultaneously and the usage often brings about many severe adverse effects such as gastrointestinal complex syndrome, upset stomach, abdominal pain, ulcers, gastrointestinal bleeding, as well as damage to the kidneys, liver, and blood system. Severe adverse side effects have been reported in one third to nearly one half of chronic NSAID users; and reports estimate 100,000 NSAID-related hospitalizations and up to 20,000 related death in United States annually (Fries J. Toward an understanding of NSAID-related adverse events: the contribution of longitudinal data. Scand. J. Rheumatol. 1996, 102(suppl):3-8; Miller J. L. Decisions loom on selective COX-2 inhibitors. Am J. Health Sys Pharm. 1999, 56:106-107).

Another type of NSAIDs, COX-2 selective inhibitors (such as celecoxib, and the withdrawn rofecoxib and valdecoxib) reduce the risk of gastrointestinal bleeding or peptic ulceration. However, these latter NSAIDs carry an elevated risk for cardiovascular disease, and some have now been withdrawn from the market. More recently, the use of dual 5-LOX/COX inhibitors (such as licofelone, tepoxalin) have been proposed as potential new drugs to treat inflammation (Martel-Pelletier J, Lajeunesse D, Reboul P, Pelletier J-P. Therapeutic role of dual inhibitors of 5-LOX and COX, selective and non-selective non-steroidal anti-inflammatory drugs. Ann Rheum Dis 2003, 62:501-509). They act by blocking the formation of both prostaglandins and leukotrienes, but do not affect lipoxin formation. Such combined inhibition avoids some of the disadvantages of selective COX-2 inhibitors and spares the gastrointestinal mucosa. Nonetheless, it is foreseen that these kinds of NSAIDs will continue to have a deleterious effects on kidneys, liver and blood system.

Corticosteroids are effective immunosuppresors, and the most effective anti-inflammatory drugs as a short-term medication, but they cannot cure arthritis. Their side effects increase as the dose and the length of the treatment increase. It is therefore important to weigh their efficacy, carefully against their side effects. The corticosteroids are mainly glucocorticoids such as cortisone and prednisolone. The glucocorticoids, although effective in reducing inflammation, can cause infection, osteoporosis, and dysfunction of the adrenal cortex. Therefore, it is recommended that glucocorticoids are not used as a long-term medication. Most doctors nowadays loath using steroids in the treatment of arthritis as their effect is modest and their adverse effects may outweigh their benefits (Barnes P. J. Anti-inflammatory actions of glucocorticoids: molecular mechanisms. Clin Sci (Lond). 1998, 94(6): 557-572).

Analgesics are commonly used to treat the pain from arthritis. They include: acetaminophen (paracetamol), opiates, diproqualone and topical lidocaine. Acetaminophen is commonly used to treat the pain from arthritis, although unlike NSAIDs, acetaminophen does not treat the inflammation. This is because it inhibits COX at central level, but not in peripheral tissues. Opioids (hydrocodone, oxycodone or morphine) may be necessary, but these should be reserved for very severe cases, and are rarely medically necessary for chronic pain.

It is believed that lifestyle plays an important role in the occurrence and development of many musculoskeletal diseases, including arthritis, and a lifestyle change may be needed for effective symptomatic relief (De Filippis L., Gulli S., Caliri A., Romano C., Munaoò F., Trimarchi G., La Torre D., Fichera C., Pappalardo A., Triolo G., Gallo M., Valentini G., Bagnato G. Epidemiology and risk factors in osteoarthritis: literature review data from "OASIS" study. Reumatismo. 2004, 56(3):169-184). Physical and emotional stress, improper diet, obesity and smoking could play a significative role in aggravating these diseases (Voigt L. F., Koepsell T. D., Nelson J. L., Dugowson C. E., Daling J. R. Smoking, obesity, alcohol consumption, and the risk of rheumatoid arthritis. Epidemiology. 1994, 5(5):525-532). On the other hand, conservative measures, such as healthy diet, weight control, appropriate rest and exercise are usually beneficial to sufferers. Nutritional changes shown to aid in the treatment of OA include decreasing saturated fat intake and using a low energy diet to reduce body fat (Wilhelmi G., Potential effects of nutrition including additives on healthy and arthrotic joints. 1. Basic dietary constituents. Zeitschrift fur Rheumatologic. 1993, 52(3):174-179; Christensen R., Astrup A., Bliddal H. Weight loss: the treatment of choice for knee osteoarthritis? A randomized trial. Osteoarthritis Cartilage. 2005, 13(1):20-27). Reducing sugar, processed foods, fatty foods and nightshade vegetables have helped many. Some doctors believe that a low fat vegetarian diet can reduce arthritis symptoms. A macrobiotic diet has been known to reduce symptoms as well. Nicotinamide (niacinamide), a derivative of vitamin B-3 which is typically used for nutritional supplementation, can be used for the treatment of arthritis. One controlled pilot study showed that subjects with OA who received nicotinamide (3 g per day) reduced their non-steroidal anti-inflammatory (NSAID) medication and increased joint mobility significantly when compared with placebo controls (Jonas W. B., Rapoza C. P., Blair W. F. The effect of niacinamide on osteoarthritis: a pilot study. Inflamm Res. 1996, 45(7):330-334). It has been shown that at high doses, nicotinamide is a potent modulator of several proinflammatory cytokines by a mechanism still not well understood (Ungerstedt J. S., Blömback M., Söderström T. Nicotinamide is a potent inhibitor of proinflammatory cytokines. Clin Exp Immunol. 2003, 131 (1):48-52). Unlike OA, there is no diet that has been shown to alleviate rheumatoid arthritis, although it has been demonstrated in RA patients that high intake (more than 3 g EPA+ DHA daily) of omega-3 fatty acids from fish oil has anti-inflammatory effects (van der Tempel H., Tulleken J. E., Limburg P. C., Muskier F. A. J., van Rijswijk. Effects of fish oil supplementation in rheumatoid arthritis. Ann. Rheum. Dis. 1990, 49(2):76-80).

The human body can produce all but two of the polyunsaturated fatty acids (PUFAs) it needs. These two, omega-6 linoleic acid (LA, 18:2ω6) and omega-3 alpha-linolenic acid (LNA, 18:3ω3), are widely distributed in plant oils. In addition, fish oils contain the longer-chain omega-3 fatty acids eicosapentaenoic acid (EPA, 20:5ω3) and docosahexaenoic acid (DHA, 22:6ω3). Scientists discovered the many benefits of EPA and DHA in the early 1970's, when Danish physicians observed that Greenland Eskimos had an exceptionally low incidence of heart disease and arthritis despite the fact that they consumed a high-fat diet (Bang H O, Dyerberg J, Nielsen A B: Plasma lipid and lipoprotein pattern in Greenlandic West-coast Eskimos. Lancet 1971, 1:1143-1145). The essential fatty acids are important in several human body systems, including immune, blood and nervous systems. High intake of oils rich in omega-3 PUFAs (n-3 PUFAs) is believed to result in a decrease in cell membrane arachidonic acid (AA) levels and a concomitant decrease in the synthesis of pro-inflammatory eicosanoids (series-2 prostaglandins, thromboxanes and series-4 leukotrienes) from AA, while substantially increasing the substrate for anti-inflammatory compounds, such as prostaglandin E3 Moreover, the decrease in the production of leukotrienes can inhibit neutrophil function and their cytotoxic activity (Simopoulos A. P. Omega-3 fatty acids in inflammation and autoimmune diseases. J Am Coll Nutr. 2002, 21(6):495-505; U.S. Pat. No. 6,485,752). The consumption of animal fats and omega-6 vegetable oils increases the AA content of cell membranes, and for this reason, the anti-inflammatory diet to treat arthritis is based on the reduction of dietary sources of AA, while increasing the intake of omega-3 PUFAs from cold-water fish and/or good quality flax seed oils. Research on inflammatory conditions report effective oral doses ranging from 1.2 to 4.6 g/day of fish oil (600 to 2300 mg/day EPA+DHA) (Wallace J. M. Nutritional and Botanical Modulation of the inflammatory cascade—eicosanoids, cyclooxygenases, and lipoxygenases—as an adjunct in cancer therapy. Int Cancer Therapies. 2002, 1(1):7-37).

Regular exercise, if possible, starting with home joint protection exercises (JPE) followed by walking or swimming, is encouraged. Regular exercise is important for maintaining joint mobility and making the joint muscles stronger (Stamm T. A., Machold K. P., Smolen J. S., Fischer S., Redlich K., Graninger W., Ebner W., Erlacher L. Joint protection and home hand exercises improve hand function in patients with hand osteoarthritis: a randomized controlled trial. Arthritis Rheum. 2002, 47 (1): 44-49). Some researches suggest that moderate alcohol consumption lowers the risk of developing arthritis (Turesson C. Increased Alcohol Intake Associated with Decreased Risk of Developing Rheumatoid Arthritis. (Abstract) Paper presented at the annual European Congress of Rheumatology. Barcelona, Spain. Jun. 13-16, 2007. European League Against Rheumatism, Jun. 15, 2007; Myllykangas-Lusojarvi, R., Aho, K., Kautiainen, H., Hakala, M. Reduced incidence of alcohol related deaths in subjects with rheumatoid arthritis. Annals of Rheumatoid Diseases, 2000, 59, 75-76). It is also known that antioxidants, including vitamins C and E in both foods and supplements, provide pain relief from OA (McAlindon T. E., Jacques P., Zhang Y., Hannan M. T., Aliabadi P., Weissman B., Rush D., Levy D., Felson D. T. Do antioxidant micronutrients protect against the development and progression of knee osteoarthritis? Arthritis Rheum 1996; 39:648-656). It has also been found in one study, that an increase in vitamin K intake reduces the prevalence of arthroses (Neogi T., Booth S. L., Zhang Y. Q., Jacques P. F., Terkeltaub R., Aliabadi P., Felson D. T. Low Vitamin K Status is Associated with Osteoarthritis in the Hand and Knee. Arthritis Rheum. Abril, 2006; 54(4): 1255-1261), however, a robust explanation for this finding has not been advanced. Ginger rhizome (Zingiber officinale) extract has been used to improve knee symptoms in OA. Ginger, is supposed, can help reduce inflammation, as it relaxes the muscles surrounding blood vessels and facilitates blood flow throughout the body (Altman R. D., Marcussen K. C. Effects of a ginger extract on knee pain in patients with osteoarthritis. Arthritis Rheum. 2001, 44(11):2531-2538). Treatments also include rest, relaxation and psychotherapy, as dealing with chronic pain can be difficult and often results in depression.

Although there are many anti-arthritis drugs in the markets, there is no very effective drug to cure or to control the progression of arthritis, especially for rheumatoid arthritis and osteoarthritis. Many of the NSAIDs have serious gastrointestinal and circulatory side effects. The DMARDs also have serious toxic effects on the liver and kidneys. The glucocorticoids, do not cure these diseases and have strong noxious effects as long-term medications. Other anti-arthritis drugs also have unclear efficiency problems, including slow action and severe side effects. In summary, there is a need for effective and side effect-free medications for arthritis and other musculoskeletal diseases that base their action on the possible causes of these diseases, and not on the symptoms or collateral disorders.

Contrary to what it is believed overall, we consider that the primary cause of arthritis and other musculoskeletal and connective tissues diseases of unknown origin is a chronic deficient blood flow to involved tissues. We have arrived at this conclusion considering that many symptoms associated with deficient blood circulation like cramps, numbness, tingling, chills, and stiffness are already present at different levels and under different circumstances among patients, long before they show the typical acute clinical manifestations of these diseases. Moreover, factors deleterious to the blood system such as smoking, obesity, sedentariness, diabetes, unbalanced nutrition, stress, depression and aging, are conditions related to increasing risk of developing or aggravating arthritis and other musculoskeletal and connective tissue diseases. On the other hand, agents that promote angiogenesis and improve the blood circulation such as exercising, application of heat, moderate consumption of alcohol, nicotinamide, copper, ginger extract, and omega-3 fatty acids have been consistently reported as effective in treating and alleviating symptoms of these diseases.

Among other factors, we consider that atherosclerosis, calcification of capillary blood vessels, and sustained vasoconstriction due to high triglycerides and/or cholesterol levels, low absorption of vitamin K, stress and depression could lead to a microvascular rarefaction, improper vascular flow and a micro-localized low-level ischemia. These conditions will induce angiogenesis in affected tissues, but this healing process will not be properly accomplished due to the same factors that promoted it. The final result of this cascade of facts is the apoptosis of damaged cells. The genetic background and the sort of affected tissues will further determine the course of the disease (as for example the form of arthritis) with regard to the intensity of the inflammation and immune responses triggered by stressed or damaged cells. Of course, under these circumstances, also possible is the development of an altered angiogenesis. It is clear that among the genetic background and physiological factors, other processes detrimental to blood circulation, such as a chronic inflammation related to injuries or infections, could trigger the development of chronic musculoskeletal and connective tissues disorders.

It is noteworthy that very recently, Dr. David L. Katz and his colleagues, analyzing the symptoms of fibromyalgia syndrome (FMS), another musculoskeletal disease of unknown etiology and pathogenesis, advanced the hypothesis that the cause of this syndrome could be a vasomotor dysregulation in muscles leading to low-level ischemia and its metabolic sequelae; and encouraged the scientific community to test their idea (Katz D. L., Greene L., Ali A., Faridi Z. The pain of fibromyalgia syndrome is due to muscle hypoperfusion induced by regional vasomotor dysregulation. Medical Hypotheses. 2007, 69(3):517-525). On the other hand, the treatment proposed for FMS is based mainly on intravenous micronutrient therapy (IVMT), administering arginine (precursor of NO production (vasodilator) and promoter of growth hormone production), vitamins (B3, B6, C), malic acid, zinc, bioflavonoids, and other nutraceuticals; and is not directed to promote the angiogenesis and blood circulation in the affected tissues as a way to definitively cure the disease (on the contrary, some of these compounds are known inhibitors of angiogenesis). It is very interesting to the present invention that one of the most controversial therapies to treat FMS (St. Amand's protocol) is based on the phosphate accumulation theory, and requires limiting the exposure of patients to salicylic acid, and to use guaifenesin to remove the excess of phosphate from the body (Kathy Longley (2004). Are phosphates the hidden enemy? (PDF). Fibromyalgia Association UK. (http://ukfmsguai.tripod.com)). However, it is well known that salicylates are potent inhibitors of prostaglandins (stimulators of angiogenesis), and guaifenesin has skeletal muscle relaxant properties, and it may also inhibit platelet aggregation (it is a possible vasodilator and blood thinner).

Good blood flow is essential to supply oxygen, nutrients and other vital factors to cells and tissues in order to maintain their survival, normal functioning and regeneration capacity. When blood circulation is impaired, or when a wound occurs, affected cells will produce and release factors that promote angiogenesis as a way to restore normal physiological conditions. Angiogenesis is the formation of new capillary, blood vessels from an existent vascular bed. Angiogenesis is a complex and tightly regulated process, where a perfect balance between factors that stimulate and inhibits this process is crucial. Physiologically, the body controls angiogenesis through a series of "on" (endogenous stimulators) and "off" (endogenous inhibitors) regulatory switches. Some endogenous stimulators and inhibitors of angiogenesis are listed in Table 1. Up-regulated angiogenesis is believed to be a causal factor in certain pathological conditions such as cancer, diabetic retinopathy, arthritis (which we refute here), psoriasis, etc.; while, down-regulated angiogenesis is found to cause coronary artery disease or impaired healing of chronic ulcers (Folkman J., Shing Y. Angiogenesis. J. Biol. Chem. 1992, 267:10931-10934; Folkman J. Angiogenesis in cancer, vascular, rheumatoid and other diseases. Net. Med. 1995, 1:27-31).

TABLE 1

Some stimulators and inhibitors of Angiogenesis.

| Stimulators | Inhibitors |
|---|---|
| Angiogenin | Tissue inhibitor of metalloprotease (TIMP-1, TIMP-2 and TMP-3) |
| Angiotropin | Plasminogen activator inhibitor-1 (PAI-1) |
| Epidermal growth factor | Interleukin-10 |
| Fibroblast growth factor (acidic and basic) | Interleukin-12 |
| Granulocyte-macrophage colony-stimulating factor | Interferon-alpha |
| Hepatocyte growth factor | Angiopoietin-2 |
| Scatter factor | Angiotensin |
| Placental growth factor | Angiotensin-II (AT2 receptor) |
| Platelet-derived growth factor-BB | Caveolins 1 and 2 |
| Tumor necrosis factor-alpha | Endostatin |
| Transforming growth factor-beta | Prolactin (16 Kd fragment) |
| Vascular endothelial growth factor | Platelet factor-4 |
| Cathepsin | Thrombospondin |
| Gelatinase A, B | Troponin-1 |
| Stromelysin | Isoflavones |
| Urokinase-type plasminogen activator | Zinc |
| Thymidine phosphorylase | |
| Farnesyl transferase | |
| Geranylgeranyl transferase | |
| Interleukin-1 | |
| Interleukin-6 | |
| Interleukin-8 | |
| Alpha/Beta 3 integrin | |
| Angiopoietin-1 | |
| Angiostatin II (ATI receptor) | |
| Endothelin (ETB receptor) | |
| Erythropoietin (EPO) | |
| Nitric oxide synthase | |
| Nitric oxide | |
| Platelet-activating factor | |
| Adiponectin | |
| Thrombopoietin | |
| Prostaglandins E1 and E2 | |
| Copper | |
| Adenosine | |
| Nicotinamide | |
| 1-Butyryl glycerol | |
| Hypoxia | |

The blockage of angiogenic stimulators and the use of angiogenesis inhibitors have been proposed as a therapeutic means to treat vascular proliferative disorders (Tai-Ping D. F. Rhys J., Roy B. Controlling the vasculature: angiogenesis, anti-angiogenesis and vascular targeting of gene therapy. TiPS 1995, 16:57-66; Pandya N. M., Dhalla N. S., Santani D. D. Angiogenesis-a new target for future therapy. Vascular Pharmacology. 2006, 44:265-274). On the other hand, it has been shown in animal models that systemic or topical application of angiogenic stimulators such as basic Fibroblast Growth Factor (bFGF), Vascular Endothelial Growth Factor (VEGF), or Transforming Growth Factor (TGF) may accelerate and improve the healing of duodenal ulcers (Folkman J., Szabo S., Stovroff M., McNeil P., Li W., Shing Y. Duodenal ulcer. Discovery of a new mechanism and development of angiogenic therapy that accelerates healing. Ann Surg. 1991, 214(4):414-427), reverse diabetic or other kinds of wound healing impairments (Phillips L. G., Abdullah K. M., Geldner P. D., Dobbins S., Ko F., Linares H. A., Broemeling L. D., Robson M. C. Application of basic fibroblast growth factor may reverse diabetic wound healing impairment. Ann Plast Surg. 1993, 31(4):331-334; Beck L. S., DeGuzman L., Lee W. P., Xu Y., Siegel M. W., Amento E. P. One systemic administration of transforming growth factor-beta 1 reverses age- or glucocorticoid-impaired wound healing. J Clin Invest. 1993, 92(6):2841-2849), or produce therapeutic benefit in cases of severe limb ischaemia, myocardial, or cerebral infarcts (Roberts A. B., Sporn M. B., Lefer A. M. Cardioprotective action of transforming growth factor-beta. Trends Cardiovasc. Med. 1993, 3:77-81; Banai S., Jaklish M. T., Shou M. Angiogenic-induced enhancement of collateral blood flow to ischemic myocardium by vascular endothelial growth factors in dogs. Circulation. 1994, 89:2183-2189; Takeshita S., Zheng L. P., Brogi E., Kearney M., Pu L. Q., Bunting S., Ferrara N., Symes J. F., Isner J. M. Therapeutic angiogenesis. A single intraarterial bolus of vascular endothelial growth factor augments revascularization in a rabbit ischemic hind limb model. J Clin Invest. 1994, 93(2):662-670). It has also been shown in an animal model that it is possible to induce angiogenesis through cell-therapy (Chen J., Zhang Z. G., Li Y., Wang L., Xu Y. X., Gautam S. C., Lu M., Zhu Z., Chopp M. Intravenous administration of human bone marrow stromal cells induces angiogenesis in the ischemic boundary zone after stroke in rats. Circ Res. 2003, 92(6):692-699). However, therapeutic angiogenesis is not free from potential harmful effects. Animal studies and clinical trials suggested hypotension is associated with both bFGF and especially VEGF administration due to nitric oxide release and arteriolar vasodilatation (Ware J. A., Simons M. Angiogenesis in ischemic heart disease. Nat. Med. 1997, 3:158-164). Other concerns associated with angiogenic growth factors include plaque angiogenesis, proliferative retinopathy and occult malignancies (Simons M., Bonnow R. O., Chronos N. A. Clinical trials in coronary angiogenesis: issues, problems, consensus: an expert panel summary. Circulation. 2000, 102:e73-e86). For these reasons, it is suggested that potent angiogenic growth factors should be used locally at high drug target level or low systemic exposure.

DETAILED DESCRIPTION OF THE INVENTION

According to our findings, we have developed principles for formulating a pharmaceutical composition for treating and preventing musculoskeletal and connective tissue diseases of unknown etiology, such as different forms of arthritis and other rheumatic conditions, based on a combination of agents that improve blood circulation in small vessels and angiogenesis promoting factors such as: vitamin K, polyunsaturated fatty acids, niacin, other smooth muscle relaxants (vasodilators) or hypolipidemic (antihyperlipidemic) agents. It is obvious that a key element when administering the herein proposed pharmaceutical composition is the ban on the use of high, repetitive doses of NSAIDs of any generation, DMARDs, corticoids and all those agents that could interfere with angiogenesis, or the normal functionality of blood circulatory system. These drugs block different steps in the biosynthesis of prostaglandins, cytokines and other angiogenic factors, as well as some of them have cytostatic and cytotoxic effects deleterious to angiogenesis. It is obvious that anti-inflammatory or immuno-modulatory agents that do not interfere with the angiogenesis process (such as interleukin-4, or treatments using Treg cells or other kind of cell therapies, for example) would be of great support when combined with the administration of the herein proposed composition for treating the above mentioned diseases.

Vitamin K is a key component in our composition. Many of the features of common chronic disorders, especially connective tissue disorders, are identical to the symptoms of vitamin K deficiencies. Unfortunately, this vitamin receives little attention, and very often its deficiency is overlooked, unless a major bleeding problem arises. This fat soluble vitamin is necessary for the synthesis of 4 of the 13 factors needed for normal blood clotting (Factors II or prothrombin, VII, IX and X). Vitamin K is also needed for the synthesis of 4 other proteins involved in blood clotting, the proteins C, S, Z and M. Blood clotting proteins called "vitamin K dependent proteins" contain glutamic acid residues, which must be carboxylated for the proteins to be activated. Vitamin K acts as a coenzyme for the enzyme gamma-glutamyl carboxylase needed for converting specific precursor proteins to their active (carboxylated) form. Two vitamin K dependent proteins in skeletal tissues include bone Gla protein (BGP or osteocalcin) and matrix gamma-carboxyglutamic acid (Gla) protein (MGP), which explains why vitamin K may, decrease the incidence or severity of osteoporosis and slow bone loss. It has been found that MGP is a potent in vivo inhibitor of arterial calcification, and for that reason an impaired carboxylation of MGP may contribute to the development or the progression of vascular disease. In fact, one study shows that impaired carboxylation of MGP is associated with intimal and medial vascular calcification, and suggests the essentiality of the vitamin K modification to the function of MGP as an inhibitor of ectopic calcification (Schurgers L. J., Teunissen K. J. F., Knapen M. H. J., Kwaijtaal M., Van Diest R., Appels A., Reutelingsperger C. P., Cleutjens J. P. M., Vermeer C. Novel conformation-specific antibodies against matrix γ-carboxyglutamic acid (Gla) protein: Undercarboxylated matrix Gla protein as marker for vascular calcification. Arterioscler Thromb Vasc Biol. 2005, 25(8):1629-1633). Moreover, it has been demonstrated in rats that arterial calcification and the resulting decreased arterial distensibility are reversible by high intake of vitamin K (Schurgers L J, Spronk H M, Soute B A, Schiffers P M, DeMey J G, Vermeer C. Regression of warfarin-induced medial elastocalcinosis by high intake of vitamin K in rats. Blood. 2007, 109(7):2823-2831).

Vitamin K is found in nature in two forms: vitamin K1, also called phylloquinone, (Phytonadione; 2-methyl-3-phytyl-1-4-naphthoquinone) is found in plants, and vitamin K2, also called menaquinone, which can be synthesized by many bacteria. Vitamin K3, menadione, is a synthetic form of this vitamin which is man-made. In addition, other vitamin K analogs have been synthesized and currently include vitamins K4, K5, K6 and K7. The richest food sources of vitamin K are greens like kale, spinach, endive, broccoli, brussels sprouts, lettuce and cabbage. After absorption, phytonadione is initially concentrated in the liver, but the concentration declines rapidly. Very little vitamin K accumulates in tissues. Although vitamin K deficiency is unlikely in healthy adults, there are many conditions that could cause an insufficiency of vitamin K, as for example: prolonged sulfa and antibiotic therapy, high intakes of salicylates, high dosages of fat soluble vitamins A and E (common in many supplements), consumption of anticoagulants like warfarin or rancid fats, malabsorptive syndromes, obstructive jaundice, alcoholism, etc. Butylated hydroxytoluenc (BHT), a common food preservative, was shown to induce vitamin K deficiencies in rats. Polyunsaturated fatty, acids decrease the absorption of vitamin K. An unbalanced diet can also contribute to a low level intake of vitamin K in the population. Not surprisingly, one study in Ireland showed that less than one third of the population met the recommended US daily intake of vitamin K. (Duggan P, Cashman K D, Flynn A, Bolton-Smith C, Kiely M Phylloquinone (vitamin K1) intakes and food sources in 18-64-year-old Irish adults. Br J Nutr. 2004, 92(1):151-158). Ethnic differences in vitamin K status of older individuals have been also reported (Yan L., Zhou B., Greenberg D., Wang L., Nigdikar S., Prynne C., Prentice A. Vitamin K status of older individuals in northern China is superior to that of older individuals in the UK. Br J Nutr. 2004, 92(6):939-945), which could explain some of the observed differences in the prevalence of rheumatic diseases between populations. It is noteworthy that elderly people, who are very often vitamin K deficient and are prone to bruise easily showing the common purpura marks, are also the people more often affected by connective tissue and musculoskeletal diseases (Booth S L, Martini L, Peterson J W, Saltzman E, Dallal G E, Wood R J. Dietary phylloquinone depletion and repletion in older women. J Nutr. 2003, 133(8):2565-2569). As it was mentioned above, low vitamin K status has also been associated with increased prevalence of OA manifestations in the hands and knees.

Toxicity does not easily occur with normal dietary intake of vitamin K, but can happen if the synthetic compound vitamin K3 is taken. Natural vitamin K is safe in doses up to 15 milligrams per day. Generally 1 to 6 milligrams daily is adequate for those showing signs of a deficiency, but if the person is taking anti-coagulant medication, he/she must consult a medical practitioner before taking a Vitamin K supplement. It has been shown that circulating undercarboxylated osteocalcin did not decrease until 300 .mu.g vitamin K1 per dav (Vermeer, C., Schurgers, L. J., Hamulyák, K., Stöcklin, E., Shearer, M. J. Effect of vitamin K intake on the stability of oral anticoagulant treatment: dose-response relationships in healthy subjects. Blood. 2004, 104(9):2682-2689), which indicates that therapeutic doses should meet or exceed that amount; preferably between 500 .mu.g and 1 mg per day.

Elson M. L. (U.S. Pat. No. 5,510,391) proposes a vitamin K mixture to be used in a topical application for the treatment of blood vessel disorders of the skin, but his composition has no relation to musculoskeletal or connective tissue diseases and does not interfere with the present invention. The use of vitamin K as a constituent of a composition for treating and preventing musculoskeletal diseases such as different forms of arthritis and other rheumatic conditions through the improvement of blood circulation is new, and constitutes part of the present invention.

To improve blood flow and circulation in patients with musculoskeletal and connective tissue diseases, it is possible to use a combination of anticoagulants, hypolipidemic agents and vasodilators. It has been demonstrated that, even at low doses (less than 1 g of EPA+DHA per day), omega-3 fatty acids reduce triglyceride-rich lipoprotein and VLDL levels in the blood, reducing whole blood viscosity. n-3 PUFAs also diminish collagen-induced platelet aggregation, mildly prolonging bleeding time (Harris W. S. Omega-3 long-chain PUFA and triglyceride lowering: minimum effective intakes. Eur Heart J. Supplements. 2001, 3(suppl.D):D59-D61; Knapp H. R. Dietary fatty acids in human thrombosis and hemostasis. Am J. Clin Nutr 1997, 65(suppl.5):1687S-1698S). Due to these natural blood-thinner properties, n-3 PUFAs are very useful for the herein proposed treatment, being their reported anti-inflammatory properties a possible collateral benefit.

At very high doses, more than 3 g/d, omega-3 fatty acids lower blood pressure through the reduction of thromboxane $A_2$ levels and/or enhancing nitric oxide production, as well as they show antiatherogenic properties and improve endothelial function. However, in view of these high levels of n-3 PUFAs are not easily achievable without facing undesirable side effects (including increasing levels of LDL-cholesterol, "bad cholesterol"), and because the proven efficacy of other nutritional factors and medications to treat hypertension and atherosclerosis, an increased intake of omega-3 fatty acids is not recommended (Kris-Etherton P. M., Harris W. S., Appel L. J. Fish consumption, fish oil, omega-3 fatty acids, and cardiovascular disease. Circulation. 2002, 106:2747-2757).

The n-3 PUFAs supplementary doses we propose to use in our treatment (0.5 g to 1 g) is around twice the WHO daily recommendation for a healthy diet. Furthermore, regarding to herein proposed treatment, it has been reported that high intake of PUFAs can interfere with vitamin K absorption, as well as will provoke a drastic reduction of arachidonic acid levels affecting the production of prostaglandin E2 and other stimulators of angiogenesis process. For this last reason, we propose in our treatment the combined supplementary intake of n-3 and n-6 PUFAs in an approximate ratio of 3:1 to 5:1 (omega-3:omega-6) by using commercially available 1.0-1.2 ml capsules of fish and plant oils containing about 50% of omega-3 and omega 6 fatty acids; and cooking with omega-6 containing plant oils rich in alpha-linolenic acid (ALA) such as flaxseed and canola oils. A different ratio between omega fatty acids could be necessary depending on individual patient conditions. This combination of oils will also be the perfect carrier for vitamin K supplements. Both components of herein proposed method of treatment should be taken together with an antioxidant like vitamin C (500 mg) to prevent the oxidation of lipids (usually PUFAs dietary supplements contain some vitamin E, but it should be remembered that high doses of vitamin E interferes with absorption of vitamin K).

n-3 PUFAs have been proposed as anti-inflammatory means and to treat coronary, diseases, but those are not the uses we propose for omega-3 fatty acids in the present invention. A composition for treating (alleviating) joint pain and stiffness of OA by using a rose-hip concentrate and fish oil has been described, but it is based on the anti-inflammatory properties of these components (U.S. Pat. No. 6,485,752), and it is not directed to improve blood circulation. Ahmad R. Kamarei and others (U.S. Pat. No. 4,879,312), have patented a method for enhancing or provoking angiogenesis administering locally effective amounts of omega-3 polyunsaturated fatty acids (from about 100 .mu.g to about 20 mg per day per subject), but these are not the doses we propose, neither the role of PUFAs in our composition. The use of polyunsaturated fatty acids as part of a composition for treating and preventing musculoskeletal and connective tissue diseases of unknown etiology through the improvement of blood circulation is new, and constitutes another embodiment of the present invention.

In order to improve blood circulation and to fight vasoconstriction, it is advisable to use a known peripheral vasodilator like niacin (nicotinic acid). Niacin is also a common hypolipidemic agent that helps reduce triglycerides and raise HDL-cholesterol ("good cholesterol"). Moreover, recently it has been show that niacin can promote angiogenesis probably through Ang1/Tie2, phosphoinositide-3-kinase/Akt, and endothelial NOS pathways (Cui X., Zacharek A., Jiang H., Roberts C., Zhang C., Lu M., Kapke A., Feldkamp C. S., Chopp M. Niaspan increases angiogenesis and improves functional recovery after stroke. Chem J. 2007, 62(1):49-58). In liver most of the niacin is converted to nicotinamide (niacinamide), a well known stimulator of angiogenesis. The recommended niacin doses to treat vascular diseases are between 300 mg and 1000 mg daily, and extended-release niacin is foreseen to give better results. Hepatic toxicity is common with higher doses of sustained-release niacin, but rare with immediate-release and extended-release niacin at doses up to 2000 mg per day (Guyton J.R. Niacin in cardiovascular prevention: mechanisms, efficacy, and safety. Curr Opin Lipidol. 2007, 18(4):415-420). The use of a vasodilator and hypolipidemic agent, such as niacin, as one of main components in a composition for treating and preventing musculoskeletal diseases that is based on the improvement of blood circulation and angiogenesis is new, and constitutes another component of the present invention.

It is obvious that niacin derivatives or other lipid-lowering drugs, such as: Atorvastatin, Fluvastatin, Lovastation, Simvastatin, etc.; fibrates, such as: Bezafibrate, Ciprofibrate, Gemfibrozil, Fenofibrate, etc.; bile acid sequestrants, such as: Colestyramine, Colestipol, Colextran, etc.; or others, such as: Dextrothyroxine, Policosanol, Ezetimibe, etc.), as well as different vasodilators (imidazoline derivatives, such as: Phentolamine, Tolazoline, etc., purine derivatives, such as: Pentoxifylline and others, ergot alkaloids, such as: Ergoloid, Nicergoline, etc., and other peripheral vasodilators such as: Phenoxybenzamine, Vincarine, Naftidrofuryl, etc.), including natural vasodilators such as: L-Arginine, Bradykinin, Ethanol, Histamine, Nitric oxide, Nitric oxide donors or agents that increase the effects of nitric oxide, Theobromine, Papaverine, Guaifenesin, etc., could also be used as components of the pharmaceutical composition herein proposed for treating and preventing musculoskeletal and connective tissue diseases. However, we prefer to use niacin and natural PUFAs for their multiple possible benefits and low or no side effects.

It will be evident for a person skilled in the art, that the administration of the composition object of the present invention will benefit from the advantages offered by concomitant topical, local or systemic administration of angiogenic stimulators (see Table 1.). Obviously, administration of VEGF, bFGF, EPO, or agents that block inhibitors of angiogenesis, could help speed up and improve the healing process when using the pharmaceutical composition object of this invention, and for this reason it constitutes another component of the present invention.

It is also obvious that administration of anti-inflammatory, and/or immuno-modulatory agents that do not interfere with angiogenesis, such as IL-4, agents that induce T regulatory cells with therapeutic effect, and cell-therapies using Treg or other kinds of cells, can be of great importance when treating patients with a long history of the disease and that extensively received NSAIDs, DMARDs, or steroids for long periods of time, because these means will help an exacerbated immunological system to return to its normal physiological state. Furthermore, these last patients will also probably need surgery to correct malformations and remove abnormal tissues. The simultaneous administration of anti-inflammatory and/or immuno-modulatory agents that do not interfere with angiogenesis, and the herein proposed pharmaceutical composition for treating and preventing musculoskeletal diseases of unknown etiology, is also new and constitutes a component of the present invention.

The regular practice of physical exercises is important for maintaining joint mobility and making the joint muscles stronger. Moreover, it is well known the great value of exercising as a vasodilator and proangiogenic agent. Moderate exercise can also help to fight pain. It is important to alternate exercising with resting periods. It is encouraged to exercise under the supervision of a physiotherapist, if possible, starting with home joint protection exercises (JPE) followed by walking or swimming. Exercising with weights every 2-3 days is also beneficial, starting with very low loads of 1 pound or less, no more than 3 sets of 10 repetitions with 1-2 minutes of rest between sets, and gradually increasing the load pound by pound every week or two. The exercise should never provoke pain in the affected body parts. After exercising, it is recommended to apply cool compresses on the affected tissues, and to use relaxation techniques. In order to treat pain and inflammation, it is recommended the use of acetaminophen (paracetamol), acupuncture, cold and/or hot compresses, and the elevation of affected body parts. The practice of physical exercises in combination with the administration of herein proposed pharmaceutical composition for treating and preventing musculoskeletal diseases of unknown etiology is also new, and constitutes a component of the present invention.

Much evidence shows that a lifestyle change is an important component of chronic disease treatment. Healthy diet (rich in fresh fruit, vegetables and fibers, and low in animal fat, etc.), proper management of physical and emotional stresses, regular exercising, adequate resting and sleeping, and a complete ban of noxious habits like smoking are factors that greatly contribute to the success of any treatment, because they will allow natural body healing processes, such as angiogenesis, to plays their role. The use of psychotherapy and antidepressants could be, in some cases, necessary due to difficulties in dealing with chronic pain.

The distinctive feature of herein proposed pharmaceutical composition for treating and preventing musculoskeletal and connective tissue diseases of unknown etiology is that it is not only directed toward symptomatic relief, but to what we believe are the true causes underlying these pathologies. Based on their symptomatology, we consider that many of these musculoskeletal and connective tissue disorders could receive a substantial benefit if treated with the herein proposed composition for the improvement of blood circulation and angiogenesis. These diseases include arthropathies and osteopathies (such as: different forms of Arthritis, Rheumatoid arthritis, Osteoarthritis, Ankylosing spondylitis, Osteoporosis, etc.), and connective and soft tissue disorders (such as: Fibromyalgia, Arteritis, Polymyositis, Myositis, Synovitis, Systemic Lupus erythematosus, Polymyalgia rheumatica etc), as well as other related pathologies that are excellent candidates to positively respond to the herein proposed pharmaceutical composition and method of treatment.

Finally, it is evident that the above mentioned therapeutic agents can be formulated in a pharmaceutical composition due their chemical compatibility, and stability in a mix. In fact, vitamin K is soluble in fish and flax seed oils (sources of n-3 and n-6 PUFAs), and niacin can be added to this mix and emulsified without affecting their pharmacological properties. Moreover, this pharmaceutical composition formulated as a medicament will greatly facilitate its application for treating musculoskeletal and connective tissue disorders, when considering that population that suffers from these diseases are mainly elderly people who usually take several medications daily. A combined product will also have the additional advantage of a lower production cost (and potentially a lower price for final clients) when comparing to the sum of costs for individual formulations of these therapeutic agents.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

REALIZATION EXAMPLE

The following example is presented by way of illustration, not of limitation.

Example 1

A Case Study 47 year old male patient with family history of rheumatoid arthritis, showed classical RA symptoms in elbows and hands according the criteria of the American College of Rheumatology (Arnett F., Edworthy S., Bloch D., McShane D., Fries J., Cooper N., Healey L., Kaplan S., Liang M., Luthra H. The American Rheumatism Association 1987 revised criteria for the classification of rheumatoid arthritis. Arthritis Rheum. 1988, 31(3): 315-24) for a period of 3 months, was orally administered with the following treatment daily: 200 .mu.g (2×100 .mu.g) of vitamin K1 (Solaray, Inc. Park City, Utah, USA), 500 mg of vitamin C and 1200 mg of Omega 3-6-9 dietary supplement (1 capsule, Jamieson Laboratories, Toronto, Canada) containing 332 mg n-3 PUFAs, 283 mg n-6 PUFAs and 173 mg n-9 PUFAs, in the morning after a breakfast that included yogurt containing bifidobacteria; and 200 .mu.g (2×100 .mu.g) of vitamin K1 (Solaray, Inc. Park City, Utah, USA), 500 mg of vitamin C and 1000 mg of Omega-3 dietary supplement (1 capsule, Jamieson Laboratories, Toronto, Canada) containing 500 mg n-3 PUFAs after dinner. This treatment was complemented with the regular practice of moderate physical exercises every 2-3 days, including exercises with weights, the application of cold or hot compresses, relaxation techniques, elevation of affected body parts, and at least 8 hours of sleep. Pain was treated with acetaminophen when needed. After 10 weeks of treatment, almost all typical symptoms of the disease were disappeared, and the patient felt only a light pain when touching the affected areas, and just occasionally some cramps that yielded to stretch and light exercises. Then, the Omega 3-6-9 supplement was removed from the treatment and 100 mg niacin was added (Rite Aid Corporation, Harrisburg, Pa., USA) once a day during a week, twice a day for another week and 3 times daily for one more week (to a final dose of 300 mg/day). At the end of week 13, patient felt no more symptoms of arthritis, and the treatment was changed to 100 .mu.g of vitamin K1, 500 mg vitamin C and 1000 mg of Omega-3 dietary supplement (1 capsule, 500 mg n-3 PUFAs) once a day, while continuing exercising regularly, as a maintenance therapy. Four months after finishing the main treatment, patient continues without any recurrence of the disease. During the treatment period, the patient took daily a multivitamin-multimineral supplement (Equate Century complete, Vita Health Products Inc., Winnipeg, MB, Canada) containing niacinamide (15 mg/tablet), Copper II oxide (2 mg/tablet), and no Zinc. The patient only received NSAIDs (ibuprofen and diclofenac) during the first 5 weeks of the disease onset without any significative beneficial result. He never took DMARDs or steroids.

CONCLUSION

In light of the detailed description of the invention and the example presented above, it can be appreciated that the several aspects of the invention are achieved.

What is claimed is:

1. A method for treating and reducing the likelihood of developing arthritis through the improvement of the processes of blood circulation and angiogenesis comprising the administration of a combination of:
   50 μg to 15 mg of Vitamin K,
   100 mg to 3 g of omega-3-polyunsaturated fatty acid,
   50 mg to 1 g of omega-6-polyunsaturated fatty acid,
   10 mg to 3 mg of niacin and
   0.1 mg to 50 mg of Copper.

2. The method of claim 1, wherein the form of vitamin K used as said therapeutic agent is selected from the group consisting of: vitamin K1, vitamin K2, and synthetic vitamin K analogs.

3. The method of claim 2, wherein said vitamin K is administered in an amount ranging from 200 .mu.g to 6 mg.

4. The method of claim 2, wherein said vitamin K is administered in an amount ranging from 300 .mu.g to 2 mg.

5. The method of claim 2, wherein said vitamin K is administered in an amount ranging from 500 .mu.g to 1 mg.

6. The method of claim 1, wherein said omega-3 polyunsaturated fatty acid is selected from the group consisting of: eicosapentaenoic acid, docosahexaenoic acid, and alpha-linolenic acid.

7. The method of claim 1, wherein said omega-3 polyunsaturated fatty acid is administered in an amount ranging from 500 mg to 1 g.

8. The method of claim 1, wherein said omega-6 polyunsaturated fatty acid is selected from the group consisting of: linoleic acid and gamma-linolenic acid.

9. The method of claim 1, wherein said omega-6 polyunsaturated fatty acid is administered in an amount ranging from 100 mg to 300 mg.

10. The method of claim 1, wherein said niacin is administered in an amount ranging from 100 mg to 1 g.

11. The method of claim 1, wherein said form of arthritis is Rheumatoid arthritis.

12. The method of claim 1, wherein said therapeutic agents are administered to a patient systemically, and/or locally, and/or topically.

13. The method of claim 12, wherein said patient is a mammal.

14. The method of claim 13, wherein said mammal is a human.

* * * * *

UNITED STATES PATENT AND TRADEMARK OFFICE
CERTIFICATE OF CORRECTION

| | |
|---|---|
| PATENT NO. | : 8,211,947 B2 |
| APPLICATION NO. | : 12/021208 |
| DATED | : July 3, 2012 |
| INVENTOR(S) | : Guillermo Selman-Housein Sosa |

It is certified that error appears in the above-identified patent and that said Letters Patent is hereby corrected as shown below:

In the Claim No. 1, Column 18, line 21, where it reads "50 mg", should read --0  mg--

In the Claim No. 1, Column 18, line 22, where it reads "3 mg", should read --3 g--

Signed and Sealed this

Thirteenth Day of November, 2012

David J. Kappos
*Director of the United States Patent and Trademark Office*